US010723028B2

(12) United States Patent
Mewes et al.

(10) Patent No.: US 10,723,028 B2
(45) Date of Patent: Jul. 28, 2020

(54) CALCULATING A CALIBRATION PARAMETER FOR A ROBOT TOOL (71) Applicant: SIEMENS HEALTHCARE GMBH, Erlangen (DE)

(72) Inventors: Philip Mewes, Nuremberg (DE); Abhinav Gulhar, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 249 days.

(21) Appl. No.: 15/827,020

(22) Filed: Nov. 30, 2017

(65) Prior Publication Data
US 2018/0147727 A1 May 31, 2018

(30) Foreign Application Priority Data

Nov. 30, 2016 (DE) .................. 10 2016 223 841

(51) Int. Cl.
*B25J 9/16* (2006.01)
*A61B 34/20* (2016.01)
(Continued)

(52) U.S. Cl.
CPC ............. *B25J 9/1692* (2013.01); *A61B 34/20* (2016.02); *A61B 34/30* (2016.02); *B25J 9/1697* (2013.01);
(Continued)

(58) Field of Classification Search
CPC ............ A61B 34/20; A61B 2034/2065; A61B 2090/3966; A61B 2017/00725;
(Continued)

(56) References Cited

U.S. PATENT DOCUMENTS 9,492,237 B2 11/2016 Kang et al.
10,335,116 B2* 7/2019 Boctor .............. A61B 34/30
(Continued)

FOREIGN PATENT DOCUMENTS

DE 102014219581 A1 9/2015
EP 1854425 A1 11/2007
(Continued)

OTHER PUBLICATIONS

Huang et al. Mobile robot localization using ceiling landmarks and images captured from an RGB-D camera, 2012, IEEE, p. 855-860 (Year: 2012).*
(Continued)

*Primary Examiner* — McDieunel Marc
(74) *Attorney, Agent, or Firm* — Laurence Greenberg; Werner Stemer; Ralph Locher (57) ABSTRACT

A method calculates a calibration parameter for a robot tool. The method is based on the reception of an image dataset from medical imaging of an image volume via a first interface. The image volume contains a part of the robot tool and the robot tool is attached to a robot. A robot dataset is received by a second interface. The robot dataset contains a position of a movable axis of the robot during the recording of the image dataset. The position and/or orientation of a marking in the image dataset are determined by a computing unit. An image-based position and/or orientation of the tool center point of the robot tool are calculated by transforming the position and/or orientation of the marking. The calibration parameter is calculated based on the robot dataset and on the image-based position and/or orientation of the tool center point via the computing unit.

23 Claims, 3 Drawing Sheets (51) Int. Cl.
*A61B 34/30* (2016.01)
*A61B 17/00* (2006.01)
*A61B 90/00* (2016.01)

(52) U.S. Cl.
CPC ............... *A61B 2017/00725* (2013.01); *A61B 2034/2059* (2016.02); *A61B 2034/2065* (2016.02); *A61B 2090/3966* (2016.02); *G05B 2219/37555* (2013.01); *G05B 2219/39016* (2013.01); *G05B 2219/39026* (2013.01); *G05B 2219/39446* (2013.01); *G05B 2219/39466* (2013.01)

(58) Field of Classification Search
CPC .............. B61B 34/30; B61B 2034/2059; B25J 9/1692; B25J 9/1697; G05B 2219/37555; G05B 2219/39016; G05B 2219/39026; G05B 2219/39446; G05B 2219/39466
See application file for complete search history.

(56) References Cited

U.S. PATENT DOCUMENTS

2007/0265527 A1 11/2007 Wohlgemuth
2008/0247506 A1* 10/2008 Maschke ............... A61B 6/12
                                                    378/15
2009/0118864 A1 5/2009 Eldridge et al.
2009/0192524 A1 7/2009 Itkowitz et al.
2013/0123799 A1 5/2013 Smith et al.
2013/0274921 A1 10/2013 Aiso
2015/0094564 A1* 4/2015 Tashman ............... A61B 6/5223
                                                    600/424
2017/0246745 A1 8/2017 Kobayashi

FOREIGN PATENT DOCUMENTS

WO    2007136768 A2    11/2007
WO    2015197100 A1    12/2015

OTHER PUBLICATIONS

Choi et al., Fast human detection for indoor mobile robots using depth images, 2013, IEEE, p. 1108-1113 (Year: 2013).*
Maric et al., Robot arm teleoperation via RGBD sensor palm tracking, 2016, IEEE, p. 1093-1098 (Year: 2016).*
Zhang et al., Applications in Computer Vision, Image Retrieval and Robotics, 2013, IEEE, p. 1-48 (Year: 2013).*
Wikipedia; https://web.archive.org/web/20160802113947/https://en.wikipedia.org/wiki/robot_calibration.

* cited by examiner

CALCULATING A CALIBRATION PARAMETER FOR A ROBOT TOOL

CROSS-REFERENCE TO RELATED APPLICATION

This application claims the benefit, under 35 U.S.C. § 119, of German patent application DE 10 2016 223 841.8, filed Nov. 30, 2016; the prior application is herewith incorporated by reference in its entirety.

BACKGROUND OF THE INVENTION

Field of the Invention

Robots are used in medical applications in particular when high precession or high endurance is required. Such applications include biopsies, radio-frequency ablations or the positioning of orthopedic screws.

The medical use of robots is frequently guided by imaging devices such as magnetic resonance tomography scanners, computed tomography scanners, ultrasound devices or X-ray devices. These are used to depict internal structures of the human body in order to position medical tools correctly.

To prevent injuries to healthy tissue, bones or organs outside the site of the operation, it is necessary to have very precise information on the position and orientation of the robot tool. Therefore, it is necessary to calibrate robot tools.

The calibration of robots following their production is known. However, this at the most enables the calibration of the position of the tool-holding fixture since robot tools are generally provided independently of the robot and have a different service life. However, medical applications require the calibration of the robot tool itself, in particular the active point of the robot tool, which is also known as the tool center point ("TCP").

Therefore, each robot tool has to be calibrated separately together with the robot. Furthermore, wear of the robot tool makes it necessary to perform the calibration at specific time intervals.

The use of a separate calibration unit to calibrate the tool center point of a robot tool is known. Herein, such calibration units contain position-determining units for example ultrasound sensors, laser interferometry or laser triangulation. However, these separate calibration units are expensive and difficult to transport. Furthermore, the performance of calibration in that operator control causes the tool center point to contact a plurality of prespecified points is known. However, this method is time-consuming and dependent upon the skills and precision of the operator.

SUMMARY OF THE INVENTION

Therefore, it is the object of the present invention to provide a method for inexpensive and precise calibration of the tool center point of a robot tool.

In the following, the inventive solution to the problem is described with respect to the claimed apparatuses and with respect to the claimed method. Features, advantages or alternative embodiments mentioned herein can also be transferred to the other claimed subject matter and vice versa. In other words, the material claims (which are, for example, directed at an apparatus) can also be developed with the features described or claimed in connection with a method. Herein, the corresponding functional features of the method are embodied by corresponding material modules.

The invention is based on the reception of an image dataset from medical imaging of an image volume by use of a first interface, wherein the image volume contains a part of the robot tool and wherein the robot tool is attached to a robot. Furthermore, a robot dataset is received by a second interface, wherein the robot dataset contains a position of at least one movable axis of the robot during the recording of the image dataset. Furthermore, the position and/or orientation of a marking in the image dataset is determined by a computing unit. Furthermore, an image-based position and/or orientation of the tool center point of the robot tool is calculated by transforming the position and/or orientation of the marking by the computing unit. Furthermore, the calibration parameter is calculated based on the robot dataset and on the image-based position and/or orientation of the tool center point by the computing unit.

The inventors have recognized that an image dataset from medical imaging can be used to calculate the calibration parameter particularly inexpensively since, as a rule, with a medical application of the robot, an imaging device is always present and, with numerous applications of the robot, a medical image dataset is used for planning and/or monitoring. Therefore, no additional image-based calibration unit is required in addition to the imaging device. Furthermore, calibration of the tool center point can be performed quickly and efficiently without modification, in particular also after each replacement of the robot tool, in particular also before each use of the robot tool. Therefore, this also enables deviations in the calibration caused by the replacement or wear of the robot tool to be taken into consideration. Furthermore, medical image data has high resolution, so that the calibration parameter can be calculated particularly precisely.

According to a further aspect of the invention, the image dataset contains a two-dimensional X-ray projection of the image volume. The inventors have recognized that two-dimensional X-ray projections can be recorded particularly quickly and inexpensively. Furthermore, X-ray image data, in particular therefore two-dimensional X-ray projections, can represent objects or features that are not accessible to imaging with visible light.

According to a further aspect of the invention, the image dataset contains a three-dimensional volume image reconstructed from a plurality of two-dimensional X-ray projections of the image volume. The plurality of X-ray projections of the image volume can in particular be recorded with respect to two different projection directions. The inventors have recognized that a three-dimensional volume image in particular also contains three-dimensional image information on the robot tool and hence three-dimensional data relating to the position and/or orientation of the marking. This enables the calibration parameter to be calculated particularly precisely.

According to a further aspect of the invention, the three-dimensional volume image is reconstructed from two-dimensional radiographic X-ray projections of the image volume. Herein, radiographic X-ray projections designate X-ray projections that were not recorded by computed tomography. The inventors have recognized that radiographic X-ray projections are sufficient for the reconstruction of a three-dimensional volume image for the precise calibration of a robot tool. At the same time, radiographic X-ray projections are less expensive and quicker to record than a computed tomography scan. Furthermore, devices for recording radiographic X-ray projections do not fully enclose the site of the examination completely and therefore facilitate the robot's access to the site of the examination.

According to a further aspect of the invention, the structure of the robot tool is depicted in the image and the marking is embodied as the structure of the robot tool. The inventors have recognized that the structure of the robot tool depicted in the image dataset is sufficient for the determination of the position and/or orientation of the robot tool and hence of the tool center point. This enables the calibration parameter to be calculated particularly favorably since no modification of the robot tool specifically for the calibration method is required.

According to a further possible aspect of the invention, the structure of the robot tool can in particular relate to an internal structure of the robot tool. The inventors have recognized that the use of the internal structure as a marking enables the position and/or orientation of the marking to be determined particularly precisely. The position and/or orientation of the marking can in particular be determined particularly precisely if the surface of the robot tool is symmetrical, but the internal structure of the robot tool breaks this symmetry. Furthermore, the position and/or orientation of the marking can in particular be determined precisely if the internal structure has high contrast in the image dataset.

According to a further aspect of the invention, the first calculation of the image-based position and/or orientation of the tool center point is performed by registering the image dataset with a three-dimensional model of the robot tool. The inventors have recognized that the registration enables the image-based position and/or orientation of the tool center point to be determined based on the position of a few distinctive points. In particular, it is not necessary to determine the position of the tool center point directly in the image dataset. In addition, registration with the three-dimensional model of the robot tool enables the influence of wear on the position and/or orientation of the tool center point to be acquired particularly accurately. Furthermore, the registration enables production-related deviations of the robot tool from the ideal shape to be identified and taken into account when determining the position and/or orientation of the tool center point.

According to a further aspect of the invention, the marking contains a plurality of marking elements, wherein the marking elements are arranged on the outside of the robot tool and/or inside the robot tool. The inventors have recognized that the dedicated marking elements can be embodied such that they can be depicted particularly accurately in the image dataset. This enables the determination of the image-based position and/or orientation of the robot tool to be particularly simple on the one hand, but also very precise on the other. The marking elements can in particular be embodied as removable from the robot tool. In the removable embodiment, it is advantageous for the marking elements to influence the use of the robot tool.

According to a further aspect of the invention, the second calculation is based on the robot dataset such that a predicted position and/or orientation of the tool center point is calculated from the robot dataset and that the calibration parameter contains the deviations of the predicted position and/or orientation from the image-based position and/or orientation. If the position and/or orientation of the tool center point are depicted as a vector, the deviation can in particular be determined as a component-by-component difference between the predicted position and/or orientation of the tool center point and the image-based position and/or orientation of the tool center point. The inventors have recognized that the deviation of the predicted position and/or orientation from the image-based position and/or orientation is the variable that can be used as the basis for the quickest and most precise performance of the calibration of the robot and/or the robot tool.

According to a further possible aspect of the invention, the robot dataset furthermore contains a speed and/or an acceleration of the at least one movable axis of the robot during the recording of the image dataset, furthermore the second calculation of the calibration parameter is based on the robot dataset such that furthermore a speed and/or an acceleration and/or an angular speed and/or an angular acceleration of the tool center point is calculated from the robot dataset and that the calibration parameter is furthermore based on the speed and/or on the acceleration and/or on the angular speed and/or on the angular acceleration of the tool center point. The inventors have recognized that the use of speed and/or acceleration data can improve the precession of the calibration, in particular if there is a temporal offset between the measurement of the robot data and the recording of the image dataset or if the second calculation of the calibration parameter has to be performed during a movement of the robot tool.

According to a further aspect of the invention, the robot dataset furthermore contains an influencing variable of an environment of the robot, wherein the influencing variable influences a measurement of the robot dataset and/or the position of the tool center point. The inventors have recognized that taking account of an influencing variable of an environment of the robot enables the calibration to be adapted particularly well to different ambient circumstances.

According to a further aspect of the invention, the influencing variable contains at least the ambient temperature, the force acting on the robot tool or the loading of the robot end-of-arm tooling. The inventors have recognized that the inclusion of the ambient temperature enables the extension the temperature-induced different extensions of the robot tool to be taken into account in the calculation of the calibration parameter. Furthermore, the inclusion of the force acting on the robot tool or the loading the robot tool enables a deformation of the robot tool to be taken into account in the calculation of the calibration parameter.

According to a further possible aspect of the invention, the robot dataset can furthermore contain an operating parameter of the robot tool, furthermore a binary calibration request can then be determined based on the operating parameter. Herein, an operating parameter can in particular relate to the operating hours of the robot tool or the age of the robot tool. The inventors have recognized that the operating parameter can be used as the basis for a particularly quick and simple decision as to whether calibration is necessary. The binary calibration request in particular enables an operator to determine that calibration is necessary and to initiate appropriate measures. This makes it possible only to perform calibration when actually necessary.

Furthermore, the invention relates to a calibration unit for calculating a calibration parameter for a robot tool comprising the following units:
a) a first interface embodied for the first reception of an image dataset from medical imaging of an image volume, wherein the image volume contains a part of the robot tool and wherein the robot tool is attached to a robot;
b) a second interface embodied for the second reception of a robot dataset, wherein the robot dataset contains a position of at least one movable axis of the robot during the recording of the image dataset;
c) a computing unit embodied for the determination of the position and/or orientation of a marking in the image dataset. The computing unit further embodied for the first calculation of an image-based position and/or orientation of the tool center point of the robot tool by transforming the position and/or orientation of the marking. The computing unit yet further embodied for the second calculation of the calibration parameter based on the robot dataset and on the image-based position and/or orientation of the tool center point.

A calibration unit of this kind can in particular be embodied to carry out the above-described method according to the invention and the aspects thereof. The calibration unit is embodied to carry out this method and the aspects thereof in that the first interface, the second interface and the computing unit are embodied to carry out the corresponding method steps. The invention furthermore relates to a robot comprising a calibration unit according to the invention.

The invention also relates to a computer program product with a computer program and a computer-readable medium. A largely software-based implementation has the advantage that existing control devices already used in the prior art can also be easily upgraded via a software update in order to operate in the inventive manner. In addition to the computer program, such a computer program product can optionally contain additional constituents, such as, for example, documentation and/or additional components including hardware components, such as, for example, hardware keys (dongles etc.) for using the software.

A robot is a universally programmable machine in particular for handling and treating objects. In the medical field, robots can be used for precise movement and insertion of surgical or imaging tools on or in a human body. A robot contains a moving unit, a robot tool and a robot control. Herein, the moving unit contains a plurality of axes, which are mechanically coupled via connecting elements. Another common technical term used for robot tool is "effector". The tool can in particular be embodied as replaceable thus enabling the robot to be configured for use with different tools. An axis can in particular be a linear axis or an axis of rotation, an axis can in particular be driven by a motor. The control is in particular embodied to control the drives of the axes such that the tool adopts a prespecified position and/or orientation.

In the medical field, a robot tool attached to a robot is in particular used to hold and position an object or to perform a manipulation on an object. Herein, the object can, for example, be an implant or the patient. A robot tool can also be embodied as a platform to which further robot tools can be attached.

The tool center point of a robot tool designates a distinctive point of the robot tool, in particular the active point of the robot tool, in particular the point that is in contact with material or tissue to be machined. Herein, the tool center point has a position and an orientation, wherein both the position and the orientation are specified by the robot tool.

Medical imaging is the recording of an image volume in particular with a magnetic resonance tomography scanner, a computed tomography scanner, an ultrasound device and/or an X-ray device. These imaging devices are known from the prior art and therefore will not be described in detail here. The image volume is the region of the area that can be depicted with the medical imaging. Herein, the image volume can in particular contain a patient, a part of a patient and/or a robot tool. An X-ray device can in particular record an X-ray projection of the image volume with respect to a projection direction. An image dataset contains at least one image that was recorded by medical imaging.

A marking is an object that can be depicted by medical imaging such that the medical imaging is able to determine an image-based position and/or orientation of the marking. In particular, the robot tool contains the marking. A marking can in particular be the structure of the robot tool, but also a part of the robot tool, which can be depicted particularly accurately by medical imaging, for example an arrangement of lead balls in medical imaging with X-rays. The structure of the robot tool can in particular contain the geometric shape of the surface, furthermore the structure can also relate to the internal structure of the robot tool.

The position of an object designates a three-dimensional position with respect to a coordinate system. The orientation of an object designates the orientation with respect to a coordinate system. Herein, the coordinate system can be defined with respect to the area of application in which the robot is located, however, it can also be defined with respect to a component of the robot, wherein the component can be moved with respect to the area of application. The coordinate system can in particular be a Cartesian coordinate system. The position and orientation of an object is also known by the technical term 'pose'. Both the position and the orientation can be depicted by a vector, in particular by a three-dimensional vector.

When reading the claim language, the following definitions apply. When the claim language recites A and/or B it means A alone, B alone or A and B. When the claim language recites at least one of A and B it means A alone, B alone or A and B. When the claim language recites at least one of A or B it means A alone, B alone or A and B.

Other features which are considered as characteristic for the invention are set forth in the appended claims.

Although the invention is illustrated and described herein as embodied in a calculating a calibration parameter for a robot tool, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

The calibration units shown here and the robot shown here are configured to carry out a method according to the invention.

Figure 1:
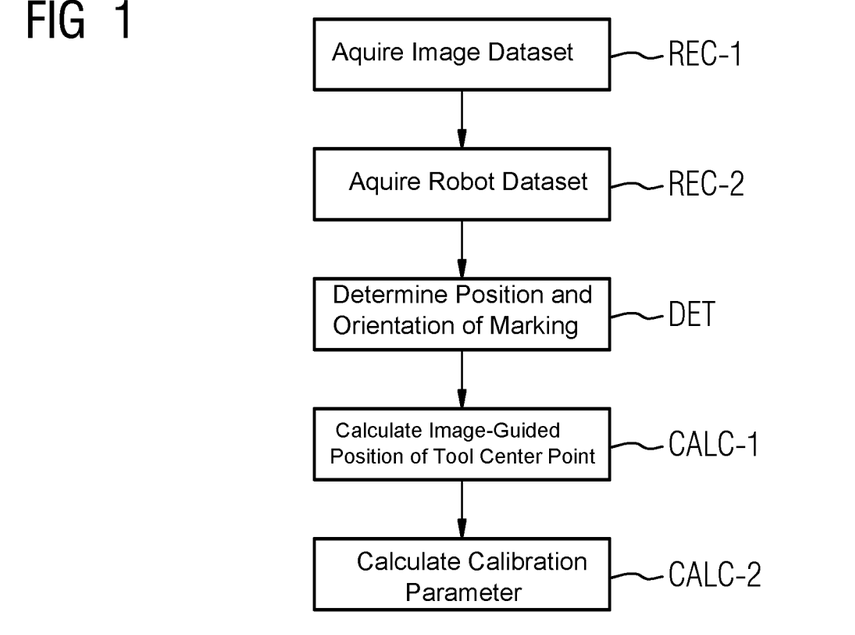
FIG. 1 is a flow diagram of a method for calculating a calibration parameter according to the invention.

A calibration parameter can be calculated with the method depicted in FIG. 1. The method contains a first reception REC-1 of an image dataset from medical imaging of an image volume by a first interface 201.1. Here, the image volume contains at least one part of a robot tool 353. Here, the image dataset is recorded with an imaging device 300, wherein, in this exemplary embodiment, the imaging device 300 is a C-arm X-ray device 300 with which X-ray projections of an image volume can be recorded from different projection directions. Here, in the exemplary embodiment shown, a plurality of X-ray projections is recorded with respect to different projection directions from which a three-dimensional volume image is reconstructed. In this exemplary embodiment, the use of X-ray projections enables the depiction of the internal structure of the robot tool 353 in the image dataset. This enables, in addition to the external shape, in particular also the internal structure of the robot tool 353 to be used as a marking. Furthermore, separate marking elements 356.1, 356.2, 356.3, which are embodied to be depicted in the X-ray imaging can be located in the interior of the robot tool.

Furthermore, the method depicted in FIG. 1 contains a second reception REC-2 of a robot dataset by a second interface 201.2, wherein the robot dataset contains a position of at least one movable axis 351.1, 351.2, 351.3 of the robot during the recording of the image dataset. A movable axis 351.1, 351.2, 351.3 can be an axis of rotation, in this case the position of the movable axis of rotation 351.1, 351.2, 351.3 contains the angle between the components connected by means of the axis of rotation. However, a movable axis 351.1, 351.2, 351.3 can also be a linear axis, in this case, the position of the movable linear axis 351.1, 351.2, 351.3 contains the set length of the linear axis. In the exemplary embodiment of the method shown, the robot dataset contains the position of all movable axes 351.1, 351.2, 351.3 of the robot. Furthermore, in this exemplary embodiment, the robot dataset contains the ambient temperature during the imaging recording, however, the robot dataset can also contain other influencing variables, for example the force acting on the robot tool due to loading.

The method depicted in FIG. 1 furthermore contains a determination DET of the position and/or orientation of a marking in the image dataset by means of the computing unit 202. In the exemplary embodiment shown, the marking is embodied by the external shape and the internal structure of the robot tool 353. Furthermore, the marking contains an arrangement of marking elements 356.1, 356.2, 356.3 in the interior of the robot tool 353. However, the marking can also only be embodied in each case by the external shape of the robot tool 353, the internal structure of the robot tool 353 or by an arrangement of marking elements 356.1, 356.2, 356.3. In the exemplary embodiment shown, the marking elements 356.1, 356.2, 356.3 are located in the interior of the robot tool 353. However, the marking elements 356.1, 356.2, 356.3 can also be located on the outside of the robot tool 353. In the exemplary embodiment shown, the marking elements are embodied by lead balls the arrangement of which determines the position and/or orientation of the marking. Also conceivable is the use of lead balls of a different size or lead objects with a different shape so that an individual marking element determines the position and/or orientation of the marking solely by its shape and alignment. Also conceivable is the use of materials other than lead, in particular materials that absorb X-rays to a greater degree than the other materials used for the construction of the robot tool 353.

Furthermore, the method depicted in FIG. 1 contains a first calculation CALC-1 of an image-based (guided) position and/or orientation 355 of the tool center point 354 of the robot tool 353 by transforming the position and/or orientation of the marking by the computing unit 202. In the exemplary embodiment shown, the marking is embodied both as a structure of the robot tool 353 and as an additional arrangement of marking elements 356.1, 356.2, 356.3. Herein, to determine the position and/or orientation of the marking, the positions of the marking elements 356.1, 356.2, 356.3 are determined in the three-dimensional image dataset. Furthermore, positions of distinctive points of the structure of the robot tool 353 are determined, for example the end point of the cross-arm 359 or the screws 358 in the fastening element 357. Herein, the relative positions of the marking elements 356.1, 356.2, 356.3 and the distinctive points of the structure of the robot tool 353 are known, for example in the form of a three-dimensional CAD model of the robot tool. The position of the marking elements 356.1, 356.2, 356.3 and the distinctive points of the structure of the robot tool 353 can therefore be registered with the CAD-model and this then enables the position and/or orientation 355 of the tool center point 354 of the robot tool 353 to be determined. Herein, the CAD-model can be adapted by the ambient temperature contained in the robot dataset in that the coefficient of thermal expansion of the materials in the robot tool 353 is taken into account.

The method depicted in FIG. 1 further contains a second calculation CALC-2 of a calibration parameter based on the robot dataset and on the image-based (guided) position and/or image-based (guided) orientation 355 of the tool center point 354 by the computing unit 202. To this end, a predicted position and/or orientation of the robot tool 353, and hence a predicted position and/or orientation of the tool center point 354, is calculated from the robot dataset in that the position and/or orientation of the tool holder 352 is determined from a known position and orientation of the robot stand 363 going beyond the measured position of the movable axes 351.1, 351.2, 351.3 and the known dimensions of the robot 350 and then the known dimensions of the robot tool 353 are taken into account. The predicted position and/or orientation of the tool center point 354 is then compared with the image-guided, actual position and/or orientation 355 of the tool center point 354 in that the component-by-component difference of the positions and/or the component-by-component difference of the orientation is determined as a calibration parameter. The robot control unit 362 can use this calibration parameter to adapt the control of the movable axes 351.1, 351.2, 351.3, for example in that the position and/or orientation is corrected by the component-by-component difference. Depending upon the design of the robot, it can also be necessary to perform the calibration with reference to a plurality of adopted positions and/or orientations of the robot tool, in particular when a plurality of robot datasets corresponds to the same predicted position and/or orientation, for example in the case of redundant axes.

The steps of the method depicted in FIG. 1 can also be performed in a sequence other than that described. For example, the second reception REC-2 can take place prior to the first reception REC-1 and the determination DET of the image-based position can take place prior to the second reception REC-2. Other sequences of the individual method steps are also possible.

Figure 2:
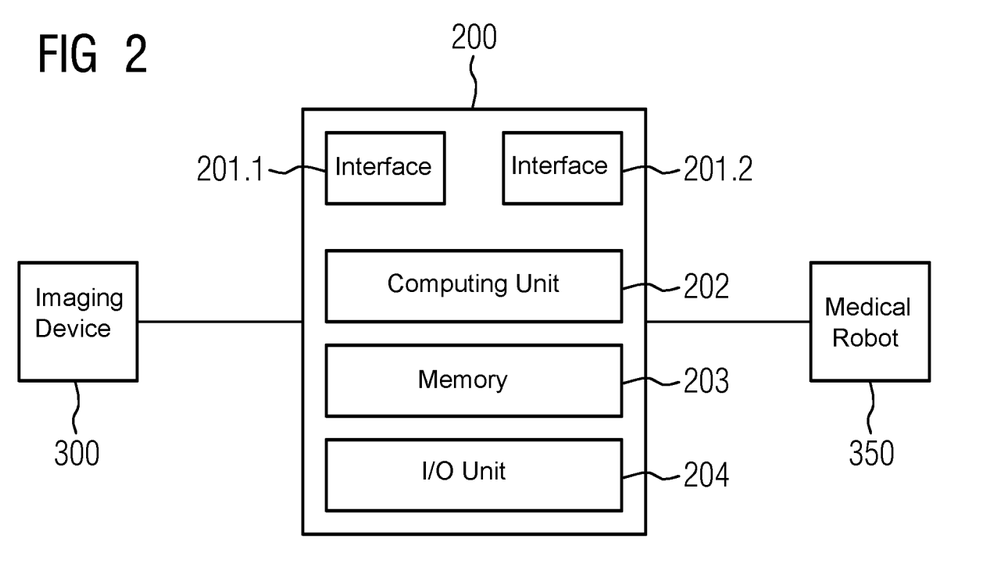
FIG. 2 is a block diagram of a calibration unit.

FIG. 2 shows a calibration unit 200 for the calculation of calibration parameters. The calibration unit 200 contains a first interface 201.1, a second interface 201.2, a computing unit 202, a storage unit 203 and an input/output unit 204 connected. The calibration unit 200 is directly connected to an imaging device 300 and a medical robot 350. However, the connection to the imaging device and/or to the medical robot could also be established by a network, for example an intranet or the internet. The calibration unit 200 shown here is embodied to carry out the method depicted in FIG. 1. Herein, the first interface 201.1 is embodied for the first reception REC-1 of an image dataset from the imaging device 300, the second interface 201.2 is embodied for the second reception REC-2 of a robot dataset from the medical robot and the computing unit 202 is embodied for the determination DET of one of the position and/or orientation of a marking in the image dataset, for the first calculation CALC-1 of an image-based position and/or image-based orientation of the tool center point of the robot tool and the second calculation CALC-2 of a calibration parameter.

The calibration unit 200 can in particular be a computer, a microcontroller or an integrated circuit. The first interfaces 201.1 and the second interface 201.2 can be a hardware or software interface (for example PCI bus, USB or Firewire). The first interface 201.1 can also be identical to the second interface 201.2. A computing unit 202 can contain a hardware element or software elements, for example a microprocessor or a so-called FPGA (abbreviation for "field programmable gate array"). A storage unit 203 can be implemented as a non-permanent random access memory (RAM) or a permanent mass memory (hard disk, USB stick, SD card, solid-state disk). The storage unit 203 can be used to store the calibration parameter. An input and output unit 204 contains at least one input unit and/or at least one output unit. In the exemplary embodiment shown, the input and output unit can be used to start the method for the calculation of the calibration parameter and/or reporting the calculation made. In the exemplary embodiment shown here, the calibration unit 200 is embodied separately from the medical robot 350. However, the calibration unit 200 can also be part of the medical robot 350 or the robot control unit 362; it can also be identical to the robot control unit 362. Alternatively, the calibration unit 200 can also be part of the imaging device 300 or the control and evaluation unit 305 of the imaging device 300.

Figure 3:
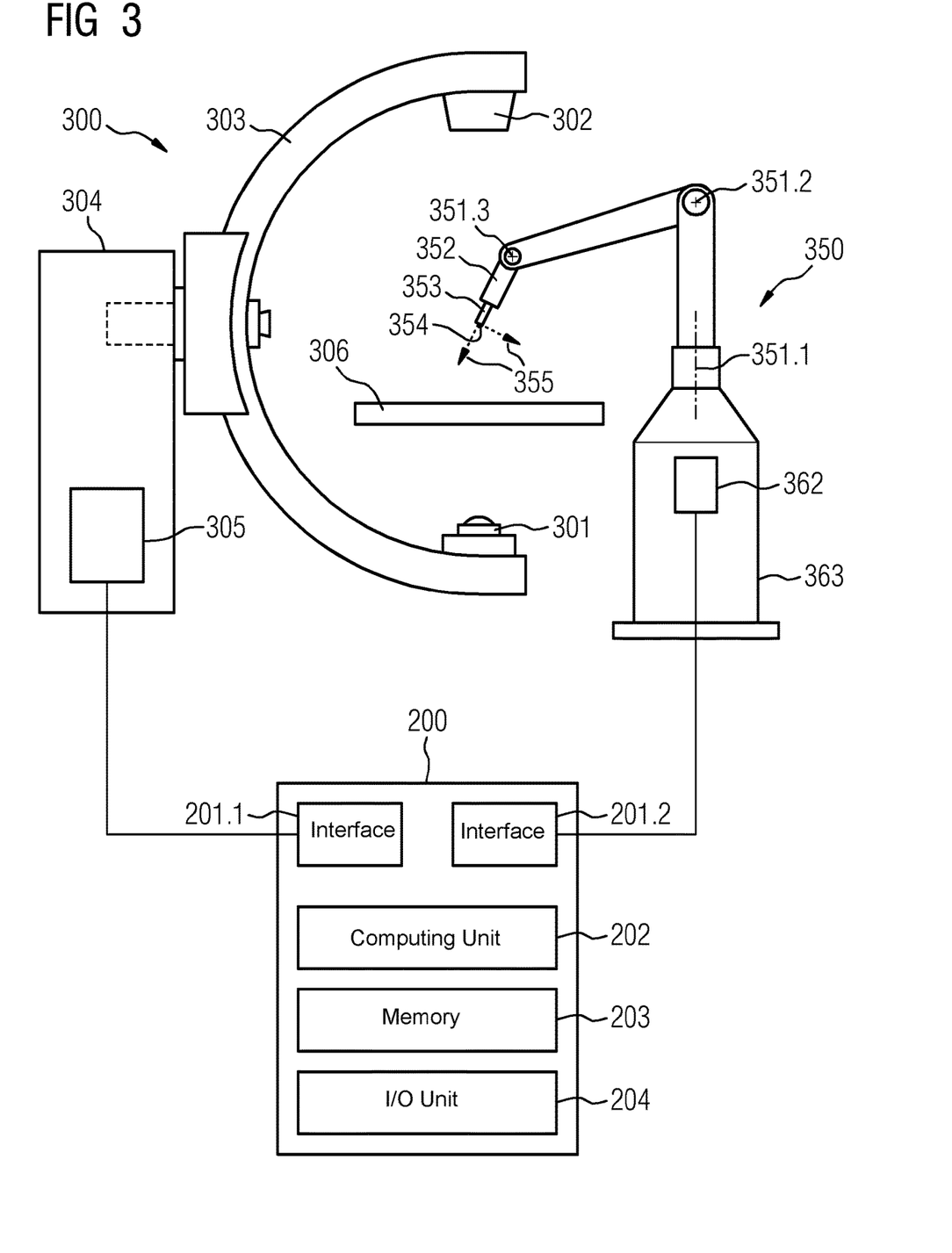
FIG. 3 is an illustration of an imaging device, a robot and a calibration unit.

FIG. 3 shows a C-arm X-ray device 300, a medical robot 350 and a calibration unit 200. The C-arm X-ray device 300 contains an X-ray source 301 for emitting X-rays. Furthermore, the C-arm X-ray device 300 contains an X-ray detector 302 for the reception of X-rays. The X-ray source 301 and the X-ray detector 302 are attached at the two different ends of the C-arm 303. The C-arm 303 of the C-arm X-ray device 300 is attached to a stand 304. The stand 304 contains drive elements configured to change the position of the C-arm 303. In particular, the C-arm 303 can be rotated about two different axes. The C-arm X-ray device further contains a control and evaluation unit 305 and a patient supporting apparatus 306. The control and evaluation unit 305 can be used to set the position of the C-arm 303. Furthermore, the control and evaluation unit 305 can be used to reconstruct two-dimensional X-ray projections and/or three-dimensional X-ray tomography scans of the site of the examination from the raw data from the X-ray detector 302.

FIG. 3 furthermore shows a medical robot 350. The medical robot 350 contains movable axes 351.1, 351.2, 351.3, which are embodied as axes of rotation in the exemplary embodiment shown. However, the movable axes 351.1, 351.2, 351.3 can also be embodied as linear axes. The medical robot 350 can contain further movable axes, which are not depicted in FIG. 3 for reasons of clarity. The movable axes 351.1, 351.2, 351.3 are embodied to position a tool-holding fixture 352 and/or a robot tool 353 freely in the site of the examination. In particular, the position and/or orientation 355 of the tool center point 354 can be changed by altering the position of the movable axes 351.1, 351.2, 351.3. The medical robot 350 further contains a robot control unit 362 and a stand 363. The robot control unit 362 is in particular embodied to set the position of the movable axes 351.1, 351.2, 351.3 such that the position and/or orientation 355 of the tool center point 354 correspond to a specified position and/or orientation. In the exemplary embodiment shown, the stand 363 is positioned fixed in the area, but the stand 363 can also be embodied as mobile.

In the exemplary embodiment shown, the first interface 201.1 of the calibration unit 200 is connected to the control and evaluation unit 305 of the C-arm X-ray device 300. Furthermore, the second interface 201.2 is connected to the robot control unit 362 of the medical robot 350. It is obviously also possible for the C-arm X-ray device 300 to contain an interface via which the calibration unit 200 is connected to the control and evaluation unit 305 of the C-arm X-ray device 300. Likewise, it is possible for the medical robot 350 to contain an interface via which the calibration unit 200 is connected to the robot control unit 362.

Figure 4:
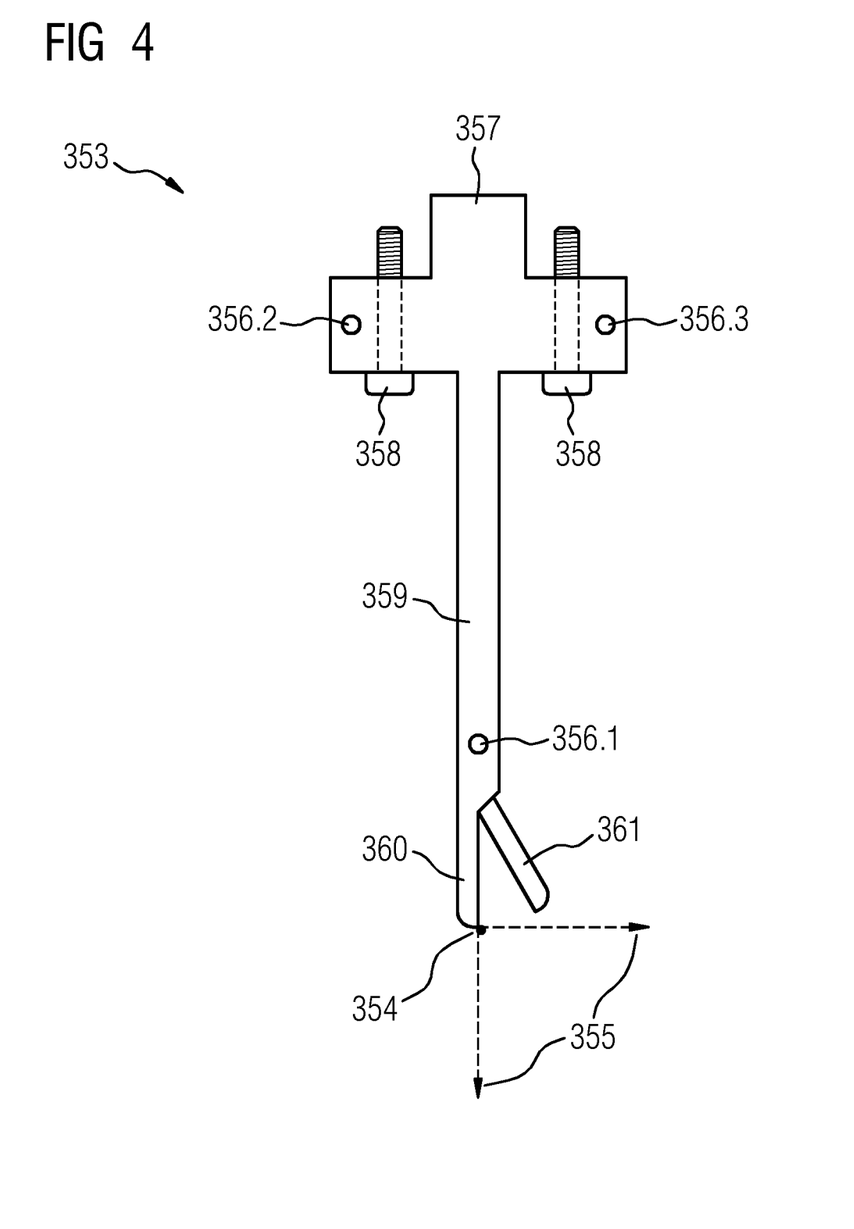
FIG. 4 is an illustration of a robot tool.

FIG. 4 shows a robot tool 353 for gripping and holding objects. The robot tool 353 consists of a fastening element 357 and a cross-arm 359. The robot tool 353 can be connected to the tool-holding fixture 352 of the medical robot by the fastening element 357. In the exemplary embodiment depicted, the connection can be secured by means of screws 358, but other connecting means are also conceivable. Embodied on the part of the cross-arm 359 facing away from the fastening element 357 is a gripper consisting of a fixed gripping element 360 and a movable gripping element 361. The movable gripping element 361 can for example be connected directly to a motor located in the cross-arm 359 or indirectly by means of a cable pull. Here, the tool center point 354 of the robot tool 353 is a point on which an object can be held. The position of the tool center point 354 is defined by the position of the fixed gripping element 360; the orientation 355 of the tool center point 354 is specified by the preferred direction of the cross-arm 359 and the direction of movement of the movable gripping element 361.

With the robot tool 353 depicted, the image-based position and/or image-based orientation of the robot tool 353, and hence the position and/or orientation 355 of the tool center point, can be determined in the image dataset in that the structure of the robot tool 353, in particular the cross-arm 259 or the movable gripping element 361, or also the screws 358, is identified in the image dataset. In the exemplary embodiment shown, the determination DET of the position and/or orientation of the robot tool 353 is facilitated by an arrangement of marking elements 356.1, 356.2, 356.3. Herein, the marking elements 356.1, 356.2, 356.3 are embodied as lead balls. Herein, one marking element 356.1 is located inside the cross-arm 359, two further marking elements 356.2, 356.3 are located inside the fastening element 357.

In order to resolve the internal structure of the robot tool 353 and hence in particular internal marking elements 356.1, 356.2, 356.3, the penetration depth of the X-rays should be of the order of magnitude of the thickness of the robot tool 353. Herein, the penetration depth is dependent on the material 353 of the robot tool and the wavelength of the X-rays used. Herein, the wavelength the X-rays can, for example, be influenced by the X-ray voltage of the X-ray source 301. If the wavelength suitable for the calibration is greater than or equal to the wavelength used in the imaging of a patient, the calibration parameter can be determined directly prior to an intervention. Otherwise, the calibration parameter can also be determined without a patient.

The invention claimed is:

1. A method for calculating a calibration parameter for a robot tool, which comprises the following method steps of:

receiving an image dataset from medical imaging of an image volume via a first interface, the image volume comprising a part of the robot tool, and the robot tool being attached to a robot;
receiving a robot dataset via a second interface, the robot dataset comprising a position of at least one movable axis of the robot during a recording of the image dataset;
determining at least one of a position and an orientation of a marking in the image dataset via a computing unit;
calculating at least one of an image-based position and an image-based orientation of a tool center point of the robot tool by transforming at least one of the position and the orientation of the marking via the computing unit; and
calculating the calibration parameter based on the robot dataset and on at least one of the image-based position and the image-based orientation of the tool center point via the computing unit.

2. The method according to claim 1, wherein the image dataset contains a two-dimensional X-ray projection of the image volume.

3. The method according to claim 1, wherein the image dataset contains a three-dimensional volume image reconstructed from a plurality of two-dimensional X-ray projections of the image volume.

4. The method according to claim 3, wherein a reconstructed three-dimensional volume image is reconstructed from two-dimensional radiographic X-ray projections of the image volume.

5. The method according to claim 1, wherein a structure of the robot tool is depicted in the image dataset and the marking is embodied as the structure of the robot tool.

6. The method according to claim 5, wherein the step of calculating at least one of the image-based position and the image-based orientation of the tool center point is performed by registering the image dataset with a three-dimensional model of the robot tool.

7. The method according to claim 1, wherein the marking contains a plurality of marking elements, and the marking elements are disposed at least on one of an outside of the robot tool and inside the robot tool.

8. The method according to claim 1, wherein the step of calculating the calibration parameter is based on the robot dataset such that at least one of a predicted position and orientation of the tool center point is calculated from the robot dataset, and that the calibration parameter contains deviations of at least one of the predicted position and orientation from at least one of the image-based position and the image-based orientation.

9. The method according to claim 1, wherein the robot dataset furthermore contains an influencing variable of an environment of the robot, the influencing variable influences a measurement of at least one of the robot dataset and the position of the tool center point.

10. The method according to claim 9, wherein the influencing variable contains at least one of the following variables:
an ambient temperature;
a force acting on the robot tool; and
loading of the robot tool.

11. A calibration unit for calculating a calibration parameter for a robot tool, the calibration unit comprising:
a first interface embodied for a first reception of an image dataset from medical imaging of an image volume, the image volume comprising a part of the robot tool and the robot tool is attached to a robot;
a second interface embodied for a second reception of a robot dataset, the robot dataset comprising a position of at least one movable axis of the robot during a recording of the image dataset; and
a computing unit embodied for determining at least one of a position and an orientation of a marking in the image dataset, said computing unit embodied for:
calculating at least one of an image-based position and image-based orientation of a tool center point of the robot tool by transforming at least one of the position and the orientation of the marking; and
calculating the calibration parameter based on the robot dataset and on at least one of the image-based position and the image-based orientation of the tool center point.

12. The calibration unit according to claim 11, wherein the image dataset contains a two-dimensional X-ray projection of the image volume.

13. The calibration unit according to claim 11, wherein the image dataset contains a three-dimensional volume image reconstructed from a plurality of two-dimensional X-ray projections of the image volume.

14. The calibration unit according to claim 13, wherein a reconstructed three-dimensional volume image is reconstructed from two-dimensional radiographic X-ray projections of the image volume.

15. The calibration unit according to claim 11, wherein a structure of the robot tool is depicted in the image dataset and the marking is embodied as the structure of the robot tool.

16. The calibration unit according to claim 15, wherein the step of calculating at least one of the image-based position and the image-based orientation of the tool center point is performed by registering the image dataset with a three-dimensional model of the robot tool.

17. The calibration unit according to claim 11, wherein the marking contains a plurality of marking elements, and the marking elements are disposed at least on one of an outside of the robot tool and inside the robot tool.

18. The calibration unit according to claim 11, wherein the step of calculating the calibration parameter is based on the robot dataset such that at least one of a predicted position and an orientation of the tool center point is calculated from the robot dataset, and that the calibration parameter contains deviations of at least one of the predicted position and the orientation from at least one of the image-based position and the image-based orientation.

19. The calibration unit according to claim 11, wherein the robot dataset furthermore contains an influencing variable of an environment of the robot, the influencing variable influences a measurement of at least one of the robot dataset and the position of the tool center point.

20. The calibration unit according to claim 19, wherein the influencing variable contains at least one of the following variables:
an ambient temperature;
a force acting on the robot tool; and
loading of the robot tool.

21. A computer program product with computer executable non-transitory instructions, which when loaded directly into a memory of a calibration unit, carrying out the steps of a method according to claim 1.

22. A non-transitory computer-readable storage medium comprising computer executable instructions to be read and executed by a calibration unit for carrying out all steps of method claim 1 when the computer executable instructions are executed by the calibration unit.

23. A robot, comprising:
a calibration unit for calculating a calibration parameter for a robot tool, said calibration unit comprising:
- a first interface embodied for a first reception of an image dataset from medical imaging of an image volume, the image volume comprising a part of the robot tool and the robot tool is attached to a robot;
- a second interface embodied for a second reception of a robot dataset, the robot dataset comprising a position of at least one movable axis of the robot during a recording of the image dataset; and
- a computing unit embodied for determining at least one of a position and an orientation of a marking in the image dataset, said computing unit embodied for:
  - calculating at least one of an image-based position and an image-based orientation of a tool center point of the robot tool by transforming at least one of the position and the orientation of the marking; and
  - calculating a calibration parameter based on the robot dataset and on at least one of the image-based position and the image-based orientation of the tool center point.

* * * * *